United States Patent
Rifa Piñol et al.

(10) Patent No.: US 7,198,779 B2
(45) Date of Patent: Apr. 3, 2007

(54) COMPOSITIONS FOR THE RELIEF OF XEROSTOMIA AND THE TREATMENT OF ASSOCIATED DISORDERS

(75) Inventors: Ana Rifa Piñol, Martorell (ES); Montserrat Mata Moliner, Sant Sadurni d'Anoia (ES)

(73) Assignee: Lacer S.A., Barcelona (ES)

( * ) Notice: Subject to any disclaimer, the term of this patent is extended or adjusted under 35 U.S.C. 154(b) by 307 days.

(21) Appl. No.: 10/490,160

(22) PCT Filed: Sep. 19, 2002

(86) PCT No.: PCT/ES02/00443

§ 371 (c)(1),
(2), (4) Date: Mar. 18, 2004

(87) PCT Pub. No.: WO03/028699

PCT Pub. Date: Apr. 10, 2003

(65) Prior Publication Data

US 2004/0247532 A1    Dec. 9, 2004

(30) Foreign Application Priority Data

Sep. 28, 2001    (ES)    ................................ 200102178

(51) Int. Cl.
  *A61K 6/00*    (2006.01)
  *A61K 8/21*    (2006.01)
(52) U.S. Cl. .................... 424/49; 424/52; 424/717; 433/216
(58) Field of Classification Search .................... None
See application file for complete search history.

(56) References Cited

U.S. PATENT DOCUMENTS 5,288,480 A * 2/1994 Gaffar et al. ................. 424/52
5,541,165 A   7/1996 Turgeon
5,651,959 A * 7/1997 Hill et al. ..................... 424/49
5,658,554 A * 8/1997 Fisher et al. ................. 424/57
5,661,171 A * 8/1997 Acharya ..................... 514/397
5,817,297 A * 10/1998 Ha et al. ...................... 424/58
6,022,528 A * 2/2000 Waterfield et al. ............ 424/49

FOREIGN PATENT DOCUMENTS

EP     0745385     12/1996
WO    WO 8909594   10/1989

* cited by examiner

*Primary Examiner*—Frederick Krass
*Assistant Examiner*—Lezah Roberts
(74) *Attorney, Agent, or Firm*—Sughrue Mion, PLLC

(57) ABSTRACT

New liquid compositions are described for the relief of the xerostomia and the treatment of associated disorders, in which the compositions contain: a) saline saliva substitute agents selected from the group consisting of sodium chloride, potassium chloride, sodium bicarbonate, monobasic potassium phosphate, and dibasic phosphate potassium; b) saliva production stimulation agents selected from the group consisting of citric acid or its alkali metal salts and malic acid or its alkali metal salts; c) oral antiseptics selected from the group consisting of triclosan, chlorhexidine and its salts, benzalkonium and its salts, and cetylpyridinium chloride; d) anticariogenic agents selected from the group consisting of fluoride sodium, sodium monofluorophosphate, and xylitol; and e) oral mucosa protective agents selected from the group consisting of vitamin E acetate, panthenol, dipotassium glycyrrhizinate and extracts of aloe vera.

The aforementioned compositions are presented in the form of mouthwashes, sprays, oral gels, and toothpastes.

14 Claims, No Drawings

COMPOSITIONS FOR THE RELIEF OF XEROSTOMIA AND THE TREATMENT OF ASSOCIATED DISORDERS

CROSS-REFERENCE TO RELATED APPLICATION

This Application is a 371 of PCT/ES02/00443, filed Sep. 19, 2002; the disclosure of which is incorporated herein by reference.

FIELD OF THE INVENTION

The present invention refers to new compositions for the relief of xerostomia or "dry mouth," which are also simultaneously useful for the treatment of disorders caused by this condition.

PRIOR ART

Xerostomia, or "dry mouth," is a symptomatic manifestation caused by a decrease in the activity of the salivary glands. The reduction in saliva formation causes individuals who suffer from this condition to have difficulty for eating, talking, chewing, etc. Even in less acute cases, the feeling of dry mouth is very unpleasant.

Xerostomia can be associated with various kinds of disorders, of which Sjörgren's syndrome is the most well-known, or can be due to exogenous causes, such as the consumption of tobacco and alcohol, the side effects of some kinds of drugs, e.g., antidepressants or diuretics, particularly in individuals receiving multiple drug therapies, or it can be due to radiotherapy and chemotherapy treatments in cancer patients.

In older individuals, xerostomia is a widespread symptom, and some authors consider that the incidence of "dry mouth" in persons over 55 years of age can be as high as 40%.

In addition, the decrease in salivary secretion typically causes associated disorders, including gingivitis, cavity formation, and the appearance of canker sores.

The numerous patents and patent applications referring specifically to preparations for alleviating xerostomia include the following:

U.S. Pat. No. 4,088,788 describes chewing gums to stimulate salivation containing a combination of an organic acid and saccharin.

U.S. Pat. No. 4,820,506 describes a liquid composition administered in aerosol spray that contains citric acid, calcium phosphate, and a food-grade sweetener, preferably aspartame.

EP396634-B1 describes a chewing gum that contains adipic acid, instead of citric acid, as the main ingredient for stimulating saliva production.

EP413427-B1 describes the specific use of xylitol, in the absence of food-grade organic acids, for the treatment of xerostomia. The edible compositions described are primarily chewing gums.

EP613684-B1 describes solid forms for the treatment of xerostomia, tablets or chewing gums, which contain polyethylene oxide as a lubricating polymer, citric acid, sources of mineral salts, and a source of fluorides.

U.S. Pat. No. 5,541,165 describes a saliva substitute composition that contains glycerin, a gum, e.g., xanthan, that can also include a buffer system based on citric acid or citrates and carbonate.

U.S. Pat. No. 5,510,122 describes a natural complete saliva composition that is treated exogenously with a disinfectant such as chlorhexidine or ionising radiation.

U.S. Pat. No. 6,159,459 describes an oral lubricant having particular usefulness for treating xerostomia based on a beta-glucan polymer.

EP745385-A2 describes a moistening composition to alleviate "dry mouth" containing an edible organic acid, such as citric or malic acid, and a source of calcium ions in phosphate form.

WO9944573 describes a tablet capable of increasing saliva production that contains an algae ingredient capable of absorbing water and a pectin-rich ingredient with a relatively low solubility.

As shown above, a significant number of proposals have been made to solve the problem of alleviating "dry mouth," which clearly indicates that there are no perfect solutions for this condition.

No solutions are observed to treat the problem globally, i.e., by also taking into account the specific treatment of disorders caused by xerostomia: gingivitis, cavity formation, and the appearance of canker sores.

Therefore, there is still a need to find alternative treatments to those described which would offer a greater range of possibilities for relief to individuals suffering from "dry mouth" and which would allow simultaneous treatment of the inherent symptoms and the subsequent disorders caused by these symptoms.

OBJECT OF THE INVENTION

The object of this invention consists of fluid, liquid or paste compositions containing saliva formation stimulation agents, saliva substitutes, antiseptics, anticariogenic agents, and oral mucosa protective agents which alleviate the symptoms of xerostomia or "dry mouth," as well as disorders associated with this condition, particularly gingivitis, cavity formation, and the appearance of canker sores.

DESCRIPTION OF THE INVENTION

The compositions contemplated in the invention are liquid or paste fluids that are characterised by comprising the following:

a) one or more saline saliva substitutes selected from the group consisting of sodium chloride, potassium chloride, sodium bicarbonate, monobasic potassium phosphate, and dibasic potassium phosphate, b) one or more saliva production stimulation agents selected from the group of citric acid or its alkali metal salts and malic acid or its alkali metal salts, c) one or more oral antiseptics selected from the group consisting of triclosan, chlorhexidine and its salts, benzalkonium and its salts, and cetylpyridium chloride.

d) one or more anticariogenic agents selected from the group consisting of fluoride sodium, sodium monofluorophosphate, and xylitol, e) one or more oral mucosa protective agents selected from the group of vitamin E acetate, panthenol, dipotassium glycyrrhizinate, and aloe vera extracts, and f) water and/or polyols acceptable for human consumption.

The compositions contemplated in the invention are for topical use and can be formulated in the form of mouthwashes, sprays, oral gels, and toothpastes, with the help of the conventional ingredients used for these topical forms, well known by those skilled in the art.

The saline saliva substitutes agents mentioned above are found in natural saliva, help provide the buffering and chelating effect that promotes remineralisation of tooth enamel, and prevent saliva pH from entering the acid region that encourages the development of cavities.

Preferably, in the compositions contemplated in the invention, the sum of the quantities of sodium chloride, potassium chloride, monobasic potassium phosphate, and dibasic potassium phosphate represents between 0.2% and 1.0% with respect to the total volume of the composition in the case of a liquid and with respect to the total weight thereof in the case of a paste (hereinafter expressed as weight/volume). Sodium bicarbonate, when present, preferably represents between 1% and 3% with respect to the total weight/volume of the composition.

Among the oral antiseptics selected, the preferred antiseptic is triclosan—a known antibacterial agent which has antiseptic activity against pathogenic microorganisms responsible for periodontitis and has recently been proven to also reduce inflammation of the gum tissues.

Preferably, the concentrations of mouthwash contained in the compositions of the invention are between 0.1% and 1.0% of antiseptic, with respect to the total weight/volume thereof.

Citric acid and malic acid cause direct stimulation of saliva secretion, although they have an adverse effect on tooth enamel due to the decrease in pH which causes demineralisation. As a result, it is preferable to formulate the aforementioned acids along with their alkali salts, which prevents an excessive decrease of pH without losing efficacy in terms of the stimulation of saliva production.

Preferably, the compositions contemplated in the invention contain between 0.1% and 0.3%, with respect to the total weight/volume thereof, of the sum of saliva production stimulation agents selected.

The anticariogenic effect of fluoride compounds, such as fluoride sodium (NaF) and sodium monofluorophosphate, also known as NaMFP, is well-known.

Preferably, the compositions contemplated in the invention contain between 0.5% and 2.0%, with respect to the total weight/volume thereof, of the sum of fluoridated compounds selected.

Xylitol is a natural sugar that is not fermented by cariogenic bacteria in acidic medium, and therefore has no cariogenic effect. In addition, it has in fact its own anticariogenic effect, as it inhibits the growth of certain bacteria present in the mouth and also helps reduce demineralization of the enamel by interfering with the transport of hydroxyapatite from the lesion to the saliva.

Preferably, the compositions contemplated in the invention contain between 1% and 10% of xylitol, with respect to the total weight/volume thereof.

Due to its buffering role which decreases acidity, bicarbonate also contributes to a anticariogenic effect.

Among the protective agents for the oral mucosa, particularly the gingival mucosa, selected for the purposes of this invention:

Vitamin E acetate improves blood circulation and inhibits inflammation, as it can inhibit the biosynthesis of prostaglandins. Therefore, gum inflammation and bleeding are reduced if vitamin E is included in daily oral hygiene. In addition, topical treatment with vitamin E accelerates the healing of oral wounds.

Panthenol is a pantothenic acid derivative that promotes the healing process by epidermal stimulation without causing sensitisation or irritation.

The extracts of aloe vera are natural products of proven efficacy that inhibit inflammation, improving the healing of wounds.

Dipotassium glycyrrhizinate is the dipotassium salt of the triterpenic heteroside extracted from the root of *Glycyrrhiza glabra* and has anti-inflammatory and healing activity, improving the conditions of the general epithelium and reducing inflammation and bleeding. In addition, dipotassium glycyrrhizinate has sweetener and surfactant properties, along with some capacity to inhibit the formation of dental plaque.

Preferably, the sum of the mucosa protective agents selected represents between 0.2% and 2.0%, calculated as pure products, with respect to the total weight/volume of the compositions contemplated in the invention.

Especially preferably, the compositions contemplated in the invention contain extract of aloe vera, in proportions between 0.01% and 0.5% expressed as concentrated pure product in solid form with respect to the total weight/volume of the composition.

The compositions contemplated in the invention are completed with water and/or polyols acceptable for human consumption, among them glycerine, sorbitol, and/or propylene glycol, as well as with other, nonessential ingredients of those conventionally used in oral liquid compositions.

As mentioned earlier, the compositions contemplated in the invention are presented in the form of mouthwashes, sprays, oral gels, and toothpastes.

As known to those skilled in the art, mouthwashes are aqueous or water-alcohol solutions for rinsing the mouth which have a well-known, conventional formulation. In addition to water, polyhydroxylated compounds such as glycerine or glycols (e.g., propylene glycol, nonionic surfactants, etc.) and other additives to improve appearance, flavour, and preservation can be included.

The sprays are compositions equal or similar to mouthwashes but dispensed in spray bottles for convenient application of the dose needed to moisten and protect the mouth without requiring subsequent rinsing.

Oral gels also include polymers that gel the compositions, which allows direct, stable application to the oral cavity. In relation to these polymers, for the purposes of this invention it is preferable to use a combination of polymers generically known as polycarbophil and carbomer, since they keep the gel structure stable for very prolonged times under extreme temperature conditions. The gels can also include a quantity of a natural, noncariogenic sweetener, such as sorbitol.

The formulation of toothpastes is well-known by those skilled in the art. In the toothpaste compositions contemplated in the invention, it is preferable to use nonionic (e.g., fatty acids esters with sugars) or amphoteric (e.g., coco-derived betaines) surfactants, since anionic surfactants have a negative effect on the delicate epithelial tissue of the gums in the cases of xerostomia. In the case of toothpastes, the use of sodium bicarbonate to neutralise oral acidity is also particularly preferred.

In addition, toothpastes can contain thickening agents such as xanthan gum, abrasive silica fillers, and other supplementary agents in addition to those normally used in the toothpaste industry.

The compositions contemplated in the invention are prepared by conventional mixing techniques, well-known to those skilled in the art, and provide fast, effective, sustained relief to individuals suffering from xerostomia, while also decreasing the incidence of cavities, gingivitis and canker sores in this type of patient.

The examples shown below are presented for the purposes of providing those skilled in the art with a sufficiently clear and complete explanation of this invention, but should not be considered limitations on the essential aspects contemplated therein, as presented in earlier sections of this description.

EXAMPLES

Example 1

Composition in the Form of Mouthwash and Spray

By mixing and dissolving the ingredients, a mouthwash is prepared with the following composition, expressed in terms of the percentage content of each ingredient with respect to the total volume of the composition:

| a) Saline saliva substitutes | |
|---|---|
| Sodium chloride | 0.09 |
| Potassium chloride | 0.06 |
| Dipotassium phosphate | 0.08 |
| Monopotassium phosphate | 0.03 |
| b) Stimulation agents for saliva production | |
| Citric acid | 0.05 |
| Malic acid | 0.04 |
| Sodium citrate | 0.10 |
| c) Antiseptic | |
| Triclosan | 0.15 |
| d) Anticariogenic agents | |
| Fluoride sodium | 0.10 |
| Sodium monofluorophosphate | 0.80 |
| Xylitol | 8.00 |
| e) Oral mucosa protective agents | |
| Aloe barbadensis powder 200:1 | 0.05 |
| Dipotassium glycyrrhizinate | 0.03 |
| Panthenol | 0.20 |
| Tocopherol acetate (vitamin E) | 0.20 |
| f) Other ingredients of the formula | |
| Glycerine | 5.00 |
| Disodium EDTA | 0.03 |
| Propylene glycol | 7.00 |
| Hydrogenated castor oil PEG-40 as nonionic surfactant (Commercial reference: CREMOPHOR RH-40) | 2.00 |
| Preservatives | <1.00 |
| Colorants, flavourings | <0.10 |
| Purified water | q.s. 100.00 ml |

Physical and chemical characterisation of the product:

Direct pH: 5.5±0.3

Density at 20° C.: 1.057 mg/ml

Example 2

Composition in the Form of an Oral Gel

By mixing the ingredients, an oral gel is prepared with the following composition, expressed in terms of the percentage content of each ingredient with respect to the total volume of the composition:

| a) Sailne saliva substitutes | |
|---|---|
| Sodium chloride | 0.09 |
| Potassium chloride | 0.06 |
| Dipotassium phosphate | 0.08 |
| Monopotassium phosphate | 0.03 |
| b) Stimulation agents for saliva production | |
| Citric acid | 0.05 |
| Malic acid | 0.05 |
| Sodium citrate | 0.05 |
| c) Antiseptic | |
| Triclosan | 0.15 |
| d) Anticariogenic agents | |
| Fluoride sodium | 0.06 |
| Sodium monofluorophosphate | 0.16 |
| Xylitol | 8.00 |
| e) Oral mucosa protective agents | |
| Aloe barbadensis powder 200:1 | 0.10 |
| Dipotassium glycyrrhizinate | 0.10 |
| Panthenol | 0.20 |
| Tocopherol acetate (vitamin E) | 0.20 |
| f) Other ingredients of the formula | |
| Polycarbophil (Commercial reference: NOVEON AA-1) | 1.00 |
| Carbomer (Commercial reference: CARBOPOL 980-NF) | 1.00 |
| Disodium EDTA | 0.20 |
| Sodium hydroxide 40% | 1.00 |
| Propylene glycol | 7.00 |
| Hydrogenated castor oil PEG-40 as nonionic surfactant (Commercial reference: CREMOPHOR RH-40) | 2.50 |
| Sorbitol | 45.00 |
| Preservatives | <1.00 |
| Colorants, flavourings | <0.10 |
| Purified water | q.s. 100.00 |

Physical and chemical characteristics:

pH (10%): 5.5±0.3

Density at 20° C.: 1.195 g/ml

Dynamic viscosity at 20° C.: D 100=8,300 mPa·s±500 mPa·s

Example 3

Composition in the Form of a Toothpaste

By mixing the ingredients, a toothpaste is prepared with the following composition, expressed in terms of the percentage content of each ingredient with respect to the total volume of the composition:

| a) Saline saliva substitutes | |
|---|---|
| Sodium chloride | 0.09 |
| Potassium chloride | 0.06 |
| Dipotassium phosphate | 0.08 |
| Monopotassium phosphate | 0.03 |
| Sodium bicarbonate | 2.00 |
| b) Stimulation agents for saliva production | |
| Sodium citrate | 0.20 |
| c) Antiseptic | |
| Triclosan | 0.30 |

-continued

| d) Anticariogenic agents | |
|---|---|
| Fluoride sodium | 0.32 |
| Sodium monofluorophosphate | 0.80 |
| Xylitol | 2.00 |
| e) Oral mucosa protective agents | |
| Aloe barbadensis powder 200:1 | 0.05 |
| Dipotassium glycyrrhizinate | 0.15 |
| Panthenol | 0.20 |
| Tocopherol acetate (vitamin E) | 0.20 |
| f) Other ingredients of the formula | |
| Xanthan gum | 0.80 |
| Glycerine | 12.00 |
| Sorbitol | 35.00 |
| Dimethicone (Commercial reference: SILICEX SH fluid) | 1.00 |
| Sodium saccharin | 0.15 |
| Polyethylene glycol 400 | 2.00 |
| Flavourings | <1.50 |
| Silica (1) (Commercial reference: SORBOSIL TC-15) | 11.00 |
| Silica (2) (Commercial reference: SORBOSIL AC-39) | 6.00 |
| Titanium dioxide | 1.50 |
| Sucrose laurate as nonionic surfactant (Commercial reference: SISTERNA LC-70) | 2.50 |
| Cocamidopropyl betaine as amphoteric surfactant (Commercial reference: TEGO BETAIN ZF) | 2.50 |
| Preservatives | <0.40% |
| Purified water | q.s. 100.00 g |

Physical and chemical characteristics:
pH (10%): 8.8±0.3
Specific gravity at 20° C.: 1.33 g/ml±0.02 g/ml
Dynamic viscosity at 20° C.: D100: 4,500 Pa·s±500 mPa·s

The invention claimed is:

1. A composition, for the relief of xerostomia and the treatment of associated disorders, consisting of:
   a) one or more saline saliva substitute agents, selected from the group consisting of sodium chloride, potassium chloride, sodium bicarbonate, monobasic potassium phosphate, and dibasic potassium phosphate,
   b) one or more saliva production stimulation agents, selected from the group consisting of citric acid or its alkali metal salts and malic acid or its alkali metal salts,
   c) one or more oral antiseptics selected from the group consisting of triclosan, chlorhexidine and its salts, benzalkonium and its salts, and cetylpyridium chloride,
   d) one or more anticariogenic agents selected from the group consisting of sodium fluoride, sodium monofluorophosphate, and xylitol,
   e) one or more oral mucosa protective agents selected from the group consisting of vitamin E acetate, panthenol, dipotassium glycyrrhizinate, and an aloe vera extract, and
   f) water and/or polyol(s) acceptable for human consumption.

2. The composition according to claim 1, wherein the sum of sodium chloride, potassium chloride, monobasic potassium phosphate, and dibasic potassium phosphate present is between 0.2% and 1.0% with respect to the total weight/volume of the composition, and the quantity of sodium bicarbonate, if present, is between 1% and 3% of the total weight/volume of the composition.

3. The composition according to claim 1, wherein said composition contains triclosan.

4. The composition according to claim 1 or 3, wherein said composition contains between 0.1% and 1.0% of antiseptic with respect to the total weight/volume of the composition.

5. The composition according to claim 1, wherein said composition contains saliva production stimulation agents in an amount of between 0.1% and 0.3%, with respect to the total weight/volume of the composition.

6. The composition according to claim 1, wherein said composition contains sodium fluoridated and/or sodium monofluorophosphate in an amount between 0.5% and 2.0%, with respect to the total weight/volume of the composition.

7. The composition according to claim 6, wherein said composition contains xylitol in an amount of between 1% and 10% with respect to the total weight/volume of the composition.

8. The composition according to claim 1, wherein said composition contains oral mucosa protective agents in an amount of between 0.2% and 2.0% with respect to the total weight/volume of the composition.

9. The composition according to claims 1 or 8, wherein the composition contains an extract of aloe vera at proportions between 0.01% and 0.5% expressed as pure concentrated product in solid form with respect to the total weight/volume of the composition.

10. The composition according to claim 1, wherein said composition is a mouthwash.

11. The composition according to claim 1, wherein said composition is a spray suitable for administration by a sprayer.

12. An oral gel composition for the relief of xerostomia and the treatment of associated disorders, consisting of:
    a) one or more saline saliva substitute agents, selected from the group consisting of sodium chloride, potassium chloride, sodium bicarbonate, monobasic potassium phosphate, and dibasic potassium phosphate,
    b) one or more saliva production stimulation agents, selected from the group consisting of citric acid or its alkali metal salts and malic acid or its alkali metal salts,
    c) one or more oral antiseptics selected from the group consisting of triclosan, chlorhexidine and its salts, benzalkonium and its salts, and cetylpyridium chloride,
    d) one or more anticariogenic agents selected from the group consisting of sodium fluoride, sodium monofluorophosphate, and xylitol,
    e) one or more oral mucosa protective agents selected from the group consisting of vitamin E acetate, panthenol, dipotassium glycyrrhizinate, and an aloe vera extract,
    f) water and/or polyol(s) acceptable for human consumption;
    g) a blend of polycarbophil polymers and carbomer, and
    h) optionally containing a noncariogenic sweetner.

13. A toothpaste composition for the relief of xerostomia and the treatment of associated disorders, consisting of:
    a) one or more saline saliva substitute agents, selected from the group consisting of sodium chloride, potassium chloride, sodium bicarbonate, monobasic potassium phosphate, and dibasic potassium phosphate,
    b) one or more saliva production stimulation agents, selected from the group consisting of citric acid or its alkali metal salts and malic acid or its alkali metal salts, c) one or more oral antiseptics selected from the group consisting of triclosan, chlorhexidine and its salts, benzalkonium and its salts, and cetylpyridium chloride,
d) one or more anticariogenic agents selected from the group consisting of sodium fluoride, sodium monofluorophosphate, and xylitol,
e) one or more oral mucosa protective agents selected from the group consisting of vitamin E acetate, panthenol, dipotassium glycyrrhizinate, and an aloe vera extract, and
f) water and/or polyol(s) acceptable for human consumption;
g) nonionic and/or amphoteric surfactants, but not anionic surfactants; and
h) optionally containing thickening agents.

14. The composition according to claim 13, wherein the composition contains sodium bicarbonate.

* * * * *